(12) United States Patent
Knapp et al.

(10) Patent No.: US 6,210,538 B1
(45) Date of Patent: Apr. 3, 2001

(54) PROCESS AND DEVICE FOR TRIGGERING AND/OR CARRYING OUT CHEMICAL REACTIONS

(75) Inventors: Günter Knapp, Sorgerweg 16, Graz (AT), A-8047; Bernhard Platzer, Graz; Michael Zischka, Stattegg, both of (AT)

(73) Assignee: Günter Knapp, Graz (AT)

( * ) Notice: Subject to any disclaimer, the term of this patent is extended or adjusted under 35 U.S.C. 154(b) by 0 days.

(21) Appl. No.: 09/220,854

(22) Filed: Dec. 28, 19

(22) Filed: 98

(30) Foreign Application Priority Data

Dec. 30, 1997 (AT) .................................... 2203/97

(51) Int. Cl.⁷ .................................................. C07C 1/00
(52) U.S. Cl. ........................................... 204/157.15
(58) Field of Search ......................... 204/157.15

(56) References Cited

U.S. PATENT DOCUMENTS

| 4,199,419 | 4/1980 | Holroyd et al. | 204/157.1 |
| 4,529,855 | 7/1985 | Fleck | 219/10.55 |

FOREIGN PATENT DOCUMENTS

| 0429814 | 6/1991 | (DE) . |
| 429814 | * 6/1991 | (EP) . |

\* cited by examiner

*Primary Examiner*—Edna Wong
(74) *Attorney, Agent, or Firm*—Jacobson, Price, Holman & Stern, PLLC

(57) ABSTRACT

In a process for triggering and/or carrying out chemical reactions by irradiating starting materials and, in particular, liquid starting materials with short-wave electromagnetic radiation emitted from at least one substance sending out short-wave electromagnetic radiation upon irradiation and excitation with long-wave electromagnetic radiation under operating conditions, the short-wave electromagnetic radiation is generated in a closed vessel arranged within the starting materials and containing the short-wave electromagnetic radiation emitting substance. A device for triggering and/or carrying out chemical reactions by irradiating with short-wave electromagnetic radiation starting materials and, in particular, liquid starting materials received in a receptacle, includes a generator for generating long-wave electromagnetic radiation as well as a vessel for receiving at least one substance sending out short-wave electromagnetic radiation upon irradiation and excitation with long-wave electromagnetic radiation under operating conditions. It is provided that the receptacle for the starting materials is designed to be permeable to long-wave electromagnetic radiation. The vessel receiving the short-wave electromagnetic radiation emitting substance, furthermore, is arranged within the receptacle and at least partially surrounded by the starting materials.

15 Claims, 4 Drawing Sheets

US 6,210,538 B1

PROCESS AND DEVICE FOR TRIGGERING AND/OR CARRYING OUT CHEMICAL REACTIONS

BACKGROUND OF THE INVENTION

1. Field of the Invention

The present invention relates to a process for triggering and/or carrying out chemical reactions by irradiating starting materials and, in particular, liquid, or mixtures of liquid and solid, starting materials with short-wave electromagnetic radiation emitted from at least one substance sending out short-wave electromagnetic radiation upon irradiation and excitation with long-wave electromagnetic radiation under operating conditions, as well as a device for triggering and/or carrying out chemical reactions by irradiating with short-wave electromagnetic radiation starting materials and, in particular liquid, or liquid and solid, starting materials received in a receptacle, comprising a generator for generating long-wave electromagnetic radiation as well as a vessel for receiving at least one substance emitting short-wave electromagnetic radiation upon irradation and excitation with long-wave electromagnetic radiation under operating conditions.

2. Prior Art

The realization of chemical reactions or processes by irradiation has been known for long with the most diverse effects being obtainable as a function of the substances used and the radiations applied. In this context, it is known to initiate or promote chemical processes by irradiation with long-wave electromagnetic waves such as, for instance, microwaves or with short-wave electromagnetic waves such as ultraviolet waves. Thus, it is known that it is possible by means of ultraviolet radiation to kill germs in food and luxury food or in biologic materials, thereby sterilizing such materials without having to apply elevated temperatures. Moreover, it is feasible to start, or keep going, specific reactions by excitation with electromagnetic waves in the UV range, whereas the use of microwaves is of particular advantage in chemistry if reactions or processes are to occur at elevated temperatures.

In many cases, however, it is particularly the combination of both long-wave and short-wave electromagnetic waves which yields particularly rapid and good results such that EP-A 0 429 814 has already proposed both a process and a device for triggering and/or promoting chemical processes, in which both long-wave electromagnetic waves, namely microwaves, and short-wave electromagnetic waves, namely ultraviolet rays, have been employed. In that process and the pertinent arrangement, it is proceeded in a manner that a receptacle for the starting materials to be treated and a gas reaction tube are arranged in a microwave oven, wherein the waves emitted from the microwave oven impinge on the gas reaction tube containing substances capable of being excited by microwaves and sending out UV rays upon excitation. The UV rays sent out by that gas reaction tube subsequently are directed onto the reaction vessel contained in the gas reaction tube or surrounded by the same and containing the substances or starting materials to be reacted. That known configuration involves the drawback that, in particular, a large-volume gas reaction tube having large dimensions suitable for surrounding an accordingly large reaction vessel must be provided and that, in particular, no uniform radiation density can be readily safeguarded over the total volume of the reaction vessel and particularly in its center at an accordingly large dimension of the reaction vessel. Another disadvantage of a gas reaction tube enclosing the reaction vessel resides in that exclusively materials that are transparent to short-wave electromagnetic radiation can be used for the reaction vessel. This constitutes a considerable limitation to the use of, in particular, pressure reaction vessels.

SUMMARY OF THE INVENTION

The present invention aims at providing a process and a device, by which it is feasible to afford directly in the reaction mixture to be reacted, or in the starting materials, as high a density of short-wave UV radiation as possible in order to be able to provide both a specific excitation and an accordingly augmented yield of reaction products.

To solve this object, the process according to the invention, departing from the initially defined prior art, is essentially characterized in that the short-wave electromagnetic radiation is generated in a closed vessel arranged within the starting materials and containing a short-wave electromagnetic radiation emitting substance. By emitting short-wave electromagnetic waves in a closed vessel arranged within the starting materials and containing the UV radiation emitting substances, an intensified UV irradiation of the reaction mixture or starting materials is feasible, thereby both improving and augmenting the reaction yields of the reaction excited by the electromagnetic radiation and offering the opportunity to carry out by the process according to the invention reactions that can only be excited by electromagnetic radiation of a specific wavelength.

In a preferred manner, and in order to provide an electromagnetic radiation of a specific wavelength, the process according to the invention is carried out such that a low pressure or negative-pressure gas is used as the short-wave electromagnetic radiation emitting substance. In order to ensure the safe ignition of the short-wave electromagnetic wave emitting gas, the process according to the invention preferably is conducted in a manner that ignition of the low pressure gas is caused by effecting an additional irradiation and excitation of a solid electrode and, in particular, a metallic electrode in the vessel receiving the low pressure gas. By providing an electrode and, in particular, a metallic electrode in the vessel receiving the low pressure gas or gas under subatmospheric pressure, an ignition spark is formed on the solid and, in particular, metallic electrode by the long-wave electromagnetic radiation, which ignition spark will safely ignite the low pressure gas contained in the vessel such that short-wave electromagnetic radiation will be continuously provided by the gas discharge of the low pressure gas.

In a preferred manner, the process according to the invention is conducted such that noble gases, methane, $CO_2$ and, in particular, gases emitting carbon bands at 193 and 247 nm are used for the low pressure gas in order to generate the short-wave electromagnetic radiation. By using noble gases, such as argon, methane or $CO_2$, as well as gases emitting carbon bands at 193 and 247 nm, a specific excitation of selected substances may be effected and a concerted reaction control may be ensured.

For as broad a scattering as possible, of the short-wave electromagnetic radiation to be emitted, the process according to the invention is further developed such that metals or metal-like substances which, under operating conditions, form volatile substances sending out short-wave electromagnetic radiation upon irradiation and excitation with long-wave electromagnetic radiation are used as the short-wave electromagnetic radiation emitting substance, wherein As, Bi, Cd, Cs, Ge, Hg, P, Pb, Rb, Sb, Se, Sn, Te, Tl or Zn, in particular, are used as metals or metal-like substances. By providing metals or metal-like substances which, under operating conditions, form volatile substances acting as a short-wave electromagnetic radiation emitting substance, it is feasible to send out the most diverse excitation energies and the most diverse wavelengths of short-wave electromagnetic radiation such that a plurality of chemical reactions may be carried out by the process according to the invention.

By said short-wave electromagnetic radiation emitting substances being contained in a vessel arranged within the reaction mixture, an intensive irradiation of the reaction mixture or starting materials is, moreover, safeguarded such that not only a plurality of reactions may be carried by the process according to the invention, but also elevated yields of reaction products may be guaranteed.

In order to be able to simultaneously emit a plurality of different wavelengths of short-wave electromagnetic radiations, the process according to the invention preferably is conducted in a manner that a mixture of at least one low pressure gas and/or at least one metal or metal-like substance is used as the short-wave electromagnetic radiation emitting substance. By providing a combination of a low pressure or negative-pressure gas and at least one metal or metal-like substance, a broader spectrum of UV bands or wave ranges can be made available, thus also ensuring the excitation of complex reaction mixtures or the promotion and maintenance of rather complex reactions.

According to the invention, microwaves are preferably used as long-wave electromagnetic radiations employed for exciting the substance(s) emitting short-wave electromagnetic radiations.

According to the invention UV rays are preferably applied as short-wave electromagnetic radiation used for exciting reaction mixtures or starting materials, since in the UV range a relatively large number of substances or reaction mixtures can be excited and a plurality of reactions can be promoted.

The processes or methods according to the invention preferably are carried out at temperatures ranging from room temperature to about 400° C. and, in particular, between 100° C. and 300° C. The process control according to the invention enables a reaction to be conducted both at room temperature and at elevated temperatures, wherein elevated temperatures may be produced directly by the long-wave electromagnetic radiation and, in particular, microwaves, thus enabling both the advantage of heating the reaction mixture and the excitation of the gas discharge of the UV radiator in one operating step.

By realizing the process with the vessel containing the short-wave electromagnetic radiation emitting substance being arranged in the interior of the starting materials, the chemical process(es) preferably may be carried out under a pressure ranging from atmospheric pressure to approximately 200 bars. In particular, the realization of reactions under elevated pressure is feasible only by arranging the vessel containing the short-wave electromagnetic radiation emitting substance in the interior of the reaction mixture, since short-wave electromagnetic radiation often cannot penetrate high-pressure vessels such that reactions under elevated pressures in the hitherto known processes have been feasible not at all or only with difficulty.

In order to solve the above-defined object, a device according to the invention for triggering and/or carrying out chemical reactions by irradiating with short-wave electromagnetic radiation starting materials and, in particular, liquid, or liquid and solid, starting materials received in a receptacle, comprising a generator for generating long-wave electromagnetic radiation as well as a vessel for receiving at least one substance sending out short-wave electromagnetic radiation upon irradation and excitation with long-wave electromagnetic radiation under operating conditions is essentially characterized in that the receptacle for the starting materials is designed to be permeable to long-wave electromagnetic radiation and the vessel receiving the short-wave electromagnetic radiation emitting substance is arranged within the receptacle and at least partially surrounded by the starting materials. Due to the vessel receiving the short-wave electromagnetic radiation emitting substance being arranged within the receptacle and at least partially surrounded by the starting materials, it is feasible by means of the device according to the invention to ensure intensive irradiation of the reaction mixture with the short-wave electromagnetic radiation so as to safeguard an elevated reaction speed and enhanced yields of the chemical reaction intended to be carried out in the receptacle.

In order to ensure as intense an irradiation as possible as well as a high radiation efficiency of the short-wave radiation emitting substance, the invention preferably is further developed such that the vessel receiving the short-wave electromagnetic radiation emitting substance is formed by a closed, substantially tubular vessel. By providing a closed substantially tubular vessel which is at least partially embedded in the reaction mixture, a largely uniform irradiation of the substances to be reacted, with the short-wave electromagnetic radiation is feasible such that starting materials contained in the receptacle can be completely reacted or excited within the shortest time possible without requiring additional whirling or stirring.

In order to ensure as complete a penetration as possible of the short-wave electromagnetic radiation through the vessel provided for the substance emitting such radiation and to optimize the radiation efficiency, the device according to the invention is further developed such that the vessel receiving the short-wave electromagnetic radiation emitting substance is made of quartz glass or UV-transparent aluminum oxide compounds and, in particular, sapphire.

In order to ensure the ignition of the gas discharge and its uniform operation in the interior of the vessel receiving the short-wave electromagnetic radiation emitting substance and as intense a UV radiation emission as possible, the device according to the invention is further developed such that said vessel comprises an additional ignition means, particularly an electrode.

In order to safely render feasible the excitation of the short-wave electromagnetic radiation emitting substance by aid of the long-wave electromagnetic radiation and not to exceed the radiation amount of long-wave electromagnetic radiation required for the excitation of the short-wave electromagnetic radiation, it is preferred that the receptacle for the starting materials is made of $SiO_2$, a plastics transparent to long-wave electromagnetic radiation such as, for instance, PTFE, TFM, PFA, or aluminum oxide compounds. By making the receptacle of a plastics transparent to long-wave electromagnetic radiation, $SiO_2$ or aluminum oxide compounds, it is feasible to pass through the receptable the long-wave electromagnetic radiation substantially unfiltered and without being attenuated by the receptacle so as to enable the excitation of the gas discharge without excessive energy input.

In order to be able to carry out in the interior of the receptable also reactions at elevated pressures or elevated temperatures, the receptacle for the starting materials according to the invention is formed by a double-walled container provided with a pressure-tight closure. In order to be able to monitor the course of a reaction and reapportion starting materials in the course of the reaction, the receptacle may be configured such that the closure is provided with a separately closeable opening, in particular for taking samples and/or apportioning starting materials.

In order to be able to carry out in the receptacle for the starting materials reactions at elevated temperatures either under normal pressure or at an elevated pressure, the receptacle for the starting materials is either enclosed on all sides by a long-wave electromagnetic radiation producing generator comprised of a microwave oven or unilaterally irradiated by microwaves focussed by means of a hollow waveguide or similar means known in microwave technology. The receptacle consequently is within a field of long-wave electromagnetic radiation and, in particular, a microwave field. The microwaves may be supplied to the receptacle for the starting materials either focussed via a resonant cavity or diffused by a "multimode cavity" (e.g., microwave oven), thereby heating the reaction mixture to the desired temperature and developing the gas discharge in the interior of the vessel receiving the short-wave electromagnetic radiation emitting substance.

BRIEF DESCRIPTION OF THE DRAWINGS

In the following, the invention will be explained in more detail by way of exemplary embodiments schematically represented in the annexed drawing. Therein.

DETAILED DESCRIPTION OF PREFERRED EMBODIMENTS OF THE INVENTION

Figure 1:
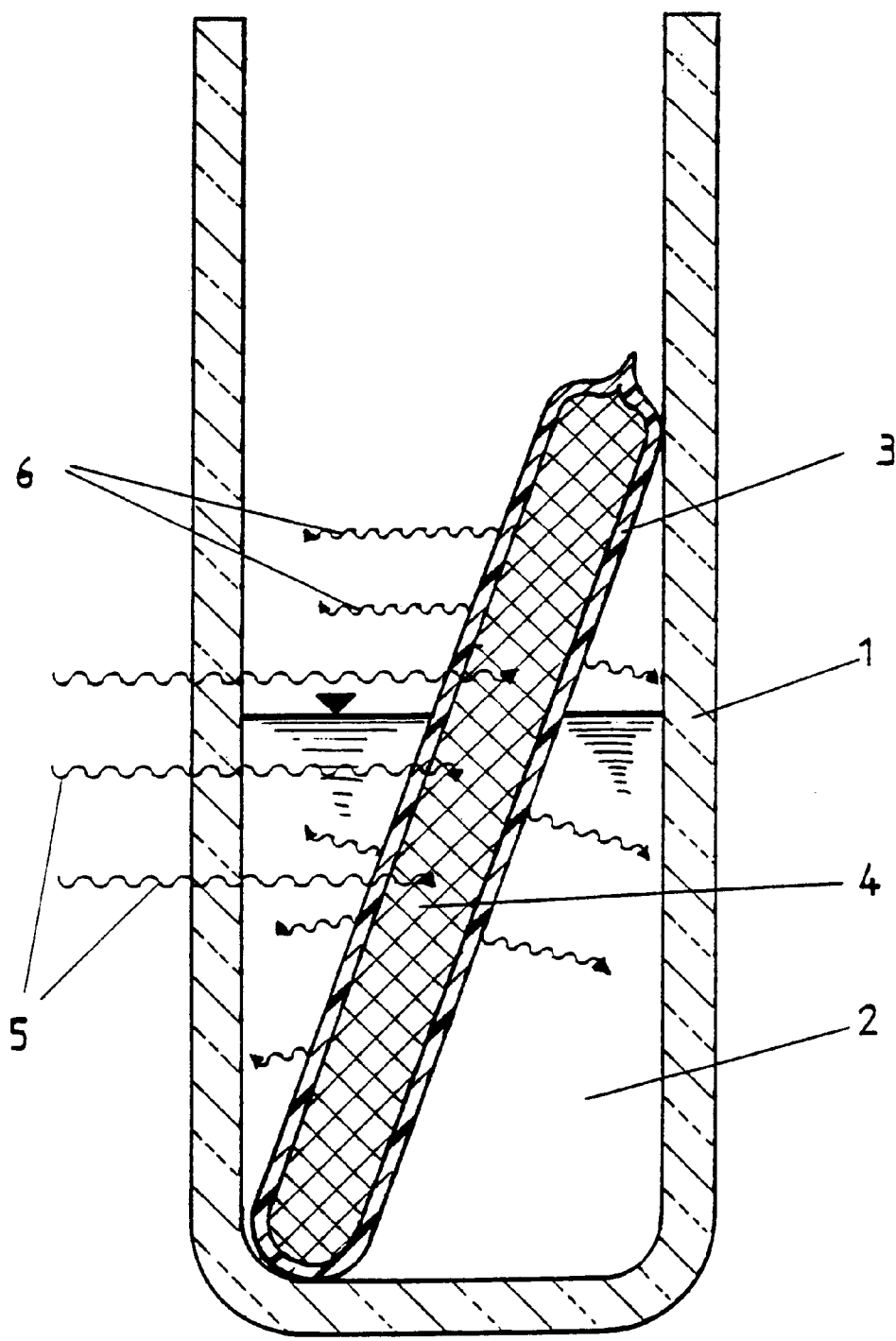
FIG. 1 is a partially sectioned view of a device according to the invention for carrying out the process according to the invention, comprising a reception container in whose interior another container for receiving a short-wave electromagnetic radiation emitting substance is arranged.

FIG. 1 depicts a receptacle generally denoted by 1 and charged with starting materials or chemical substances to be reacted, which are schematically indicated by 2. The receptacle 1 is made of a material permeable to long-wave electromagnetic radiation and, in particular, a material permeable to microwaves, such as $SiO_2$, microwave-permeable plastics or special aluminum oxides. In the interior of the receptacle 1, and partially immersed in the reaction mixture or starting materials 2, there is arranged a gas-tightly closed vessel 3 in whose interior is contained the short-wave electromagnetic radiation emitting substance, such as a noble gas, or substances emitting UV radiation under operating conditions, such as metals or metal compounds, which are schematically indicated by 4 in FIG. 1. In the operating state, long-wave electromagnetic radiation 5 emitted from a generator not illustrated and, in particular, comprised of microwaves impinges on the receptacle 1, penetrating the latter on account of the materials selected for the open container 1 and likewise being able to pass through the vessel 3 for the short-wave electromagnetic radiation emitting substance arranged in the interior of the receptacle 1. The vessel 3 in the instant case is permeable not only to long-wave electromagnetic radiation 5, but also to UV or short-wave electromagnetic radiation 6 sent out in its interior. By the long-wave electromagnetic radiation 5 passing through the receptacle 1 and the vessel 3, the substance contained in the interior of vessel 3 is excited to emit short-wave electromagnetic radiation 6, which after passing through the wall of the vessel 3 directly impinges on the reaction mixture 2, thereby ensuring particularly intense UV irradiation of the reaction mixture or starting materials 2. Any shape and any number of receptacles 1 arranged in the arrangement for excitation by long-wave electromagnetic radiation 5 not illustrated may be envisaged, since the excitation of the reaction mixture 2 merely is determined by the substances contained in the vessel 3 and the UV rays emitted from the same.

Figure 2:
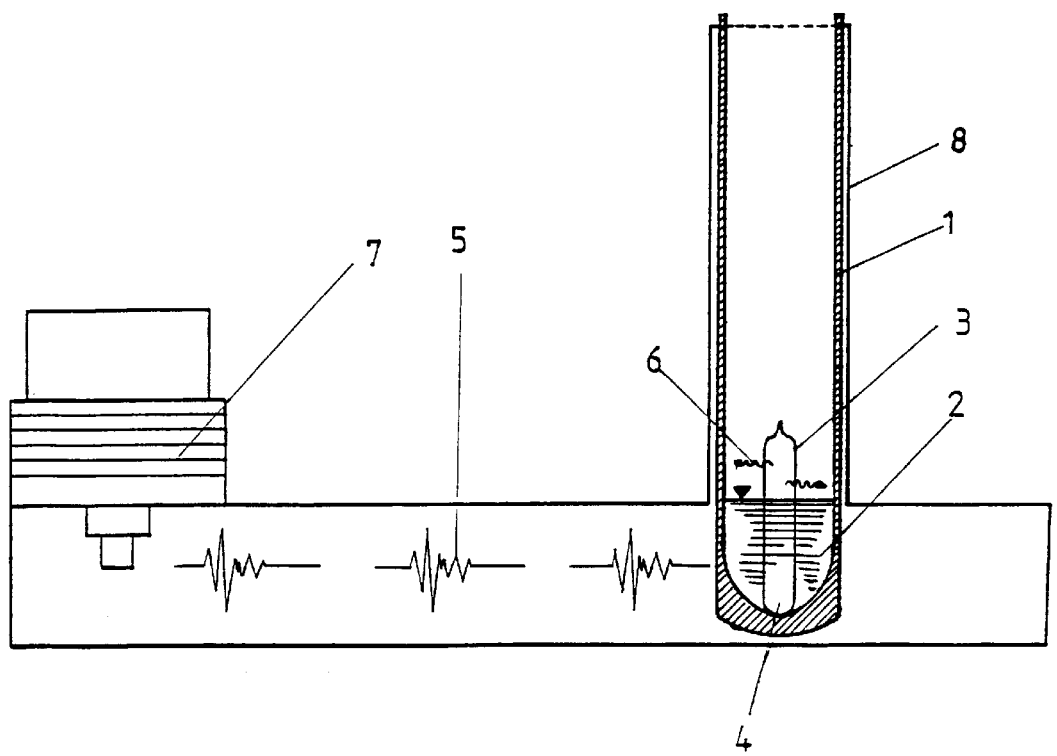
FIG. 2 is a schematic side view of a modified embodiment of a device according to the invention with a means for excitation with long-wave electromagnetic radiation, in particular microwaves, being schematically illustrated in addition.

FIG. 2 again depicts a receptacle denoted by 1 in a schematically illustrated arrangement intended to emit long-wave electromagnetic radiation 5 and, in particular, microwaves. In that arrangement, a generator 7, in particular a magnetron, sends out microwaves 5 which, focussed by a hollow waveguide, after passage through the receptacle 1 and vessel 3 excite the substance contained in the interior of the vessel 3 to emit short-wave electromagnetic radiation 6. The receptacle 1 is arranged in an open sleeve 8, the system according to FIG. 2 being intended for operation under normal pressure. The arrangement according to FIG. 2 allows for operation at temperatures ranging between room temperature and the boiling temperature of the reaction mixture.

Figure 3:
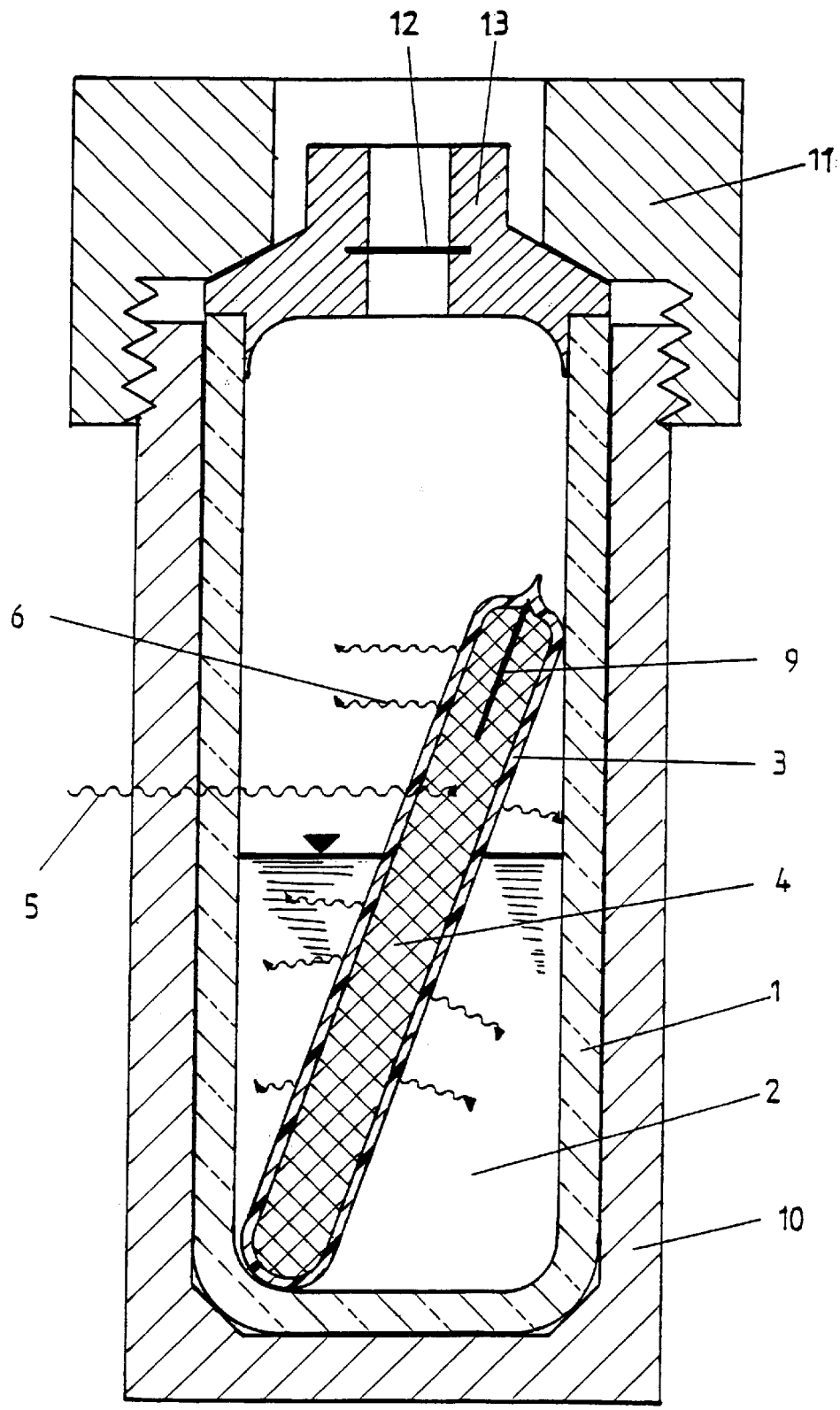
FIG. 3 is a partially sectioned view through another embodiment of the device according to the invention with the receptacle for the starting materials to be reacted being positioned within a pressure vessel.

FIG. 3 represents another sectional view of a receptacle 1 for receiving chemical reaction mixtures 2 with the reference numerals of FIG. 1 having been taken over into the illustration according to FIG. 3 unchanged. In the interior of the reaction mixture 2 there is again provided a vessel 3, which contains substances 4 capable of being excited by long-wave electromagnetic radiation 5, which, upon excitation, emit the short-wave electromagnetic radiations schematically indicated by 6, in particular UV radiations. In order to ensure the safe excitation of the substances 4 contained within the vessel 3 and assist in their ignition, the vessel 3 is equipped with an ignition electrode 9, in particular a metallic ignition electrode, which, upon excitation with long-wave electromagnetic radiation 5 is capable of igniting, and hence exciting to send out UV rays 6, the substances 4 contained in the vessel 3. The receptacle 1 according to FIG. 3, furthermore, is surrounded by a second container 10 made of a material permeable to long-wave electromagnetic radiation 5 and configured so as to be suitable also for reactions proceeding under elevated pressure in the receptacle 1. The additional container 10 is provided with a schematically indicated pressure-tight closure 11 such that, by the device according to FIG. 3, reactions not only at elevated temperatures but also at elevated pressures may be carried out, which at the same time require excitation by short-wave electromagnetic radiation 6 and, in particular, UV radiation in order to be carried out. In order to drain any inadmissible reaction pressure from the receptacle 1, a bursting disc 12 is provided in the lid 13 and the lid 13 is pressed on the receptacle 1 by a spring so that the lid will be opened by excess pressure.

Figure 4:
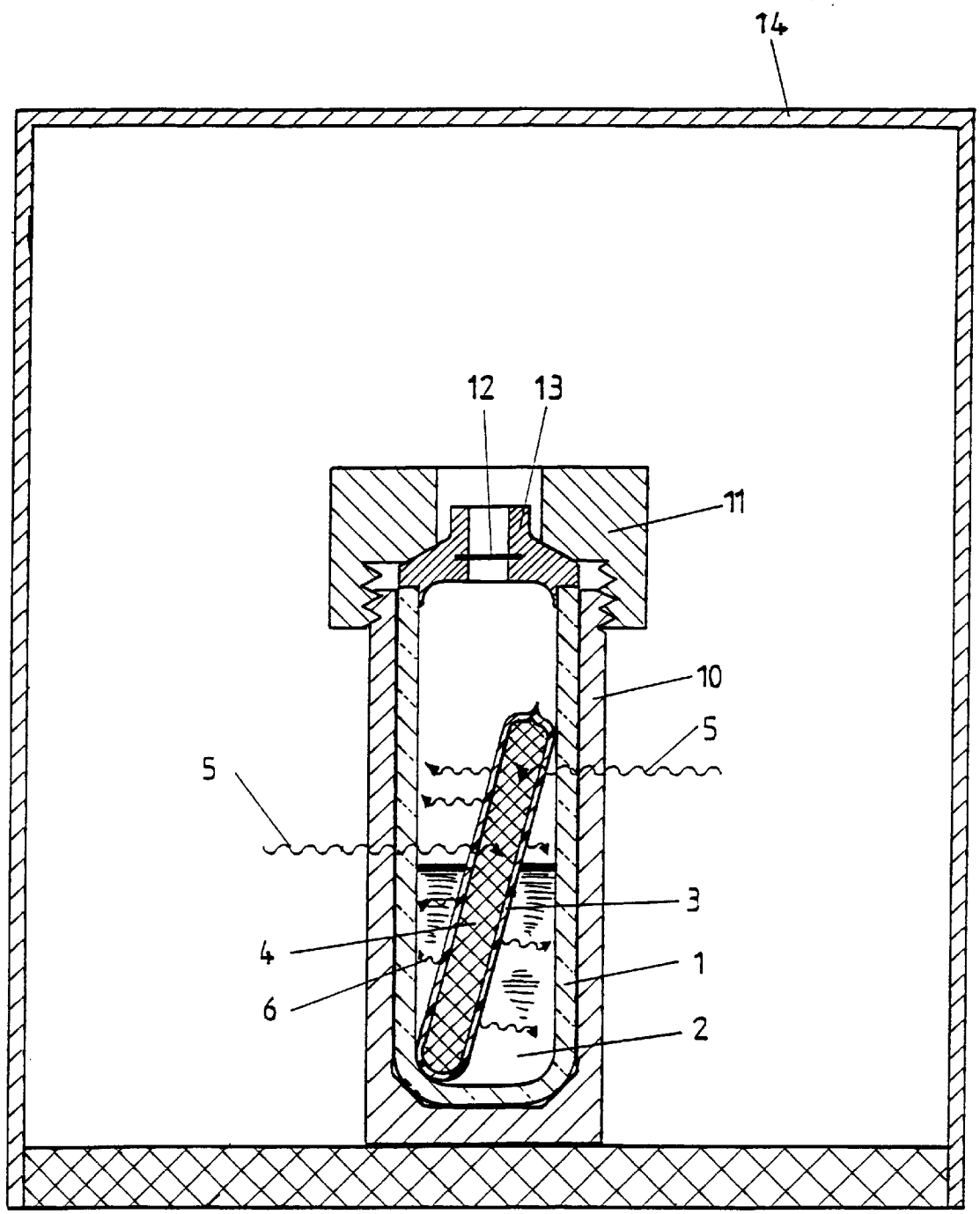
FIG. 4 is a further schematic sectional view through a device according to the invention, in which the pressure vessel of FIG. 3 is arranged in a usual microwave oven schematically illustrated.

Reactions with containers according to FIG. 3 usually are carried out in current microwave ovens as illustrated in FIG. 4, the oven in FIG. 4 being schematically indicated by 14.

Due to the excitation of a reaction mixture 2 by means of vessels 3 directly arranged within the reaction mixture 2 and containing substances 4 suitable for sending out UV radiation or short-wave electromagnetic radiation 6, such as noble gases or metal compounds volatile under operating conditions and emitting UV bands, as provided by the invention, it is feasible to afford directly in the reaction mixture or starting materials 2 a particularly high radiation density of short-wave radiation and, in particular, UV rays 6, thus ensuring as rapid as possible and, in particular, as complete as possible the reaction of the reaction mixture 2 at any desired operating conditions. The gas discharge in the interior of the vessel 3 causes the microwave radiation 5 to be focussed on the reaction mixture 2 within the receptacle 1 and on the vessel 3 containing the UV radiation emitting substances 4.

What is claimed is:

1. A process for triggering and/or carrying out chemical reactions by irradiating starting materials with short-wave electromagnetic radiation emitted from at least one substance sending out short-wave electromagnetic radiation upon irradiation and excitation with long-wave electromagnetic radiation under operating conditions, said starting materials being placed in a receptacle, said receptacle allowing long-wave electromagnetic radiation to pass therethrough while preventing penetration of short-wave electromagnetic radiation, the short-wave electromagnetic radiation being generated in a closed vessel arranged within the starting materials and containing the short-wave electromagnetic radiation emitting substance.

2. A process according to claim 1, wherein a low pressure gas is used as the short-wave electromagnetic radiation emitting substance.

3. A process according to claim 2, wherein ignition of the low pressure gas is caused by effecting an additional irradiation and excitation of a solid electrode in the closed vessel receiving the low pressure gas.

4. A process according to claim 2, wherein noble gases, methane, $CO_2$ and gases emitting carbon bands at 193 and 247 nm are used for the low pressure gas in order to generate the short-wave electromagnetic radiation.

5. A process according to claim 1, wherein metallic substances which, under said operating conditions, form volatile substances sending out said short-wave electromagnetic radiation upon irradiation and excitation with said long-wave electromagnetic radiation are used as the short-wave electromagnetic radiation emitting substance.

6. A process according to claim 5, wherein As, Bi, Cd, Cs, Ge, Hg, P, Pb, Rb, Sb, Se, Sn, Te, Tl or Zn are used as the substances.

7. A process according to claim 1, wherein a mixture of at least one low pressure gas and/or at least one metal containing substance is used as the short-wave electromagnetic radiation emitting substance.

8. A process according to claim 1, wherein microwaves are used to generate said long-wave electromagnetic radiation.

9. A process according to claim 1, wherein UV rays are used as said short-wave electromagnetic radiation.

10. A process according to claim 1, wherein the chemical reactions are carried out at temperatures ranging from room temperature to about 400° C.

11. A process according to claim 1, wherein the chemical reactions are carried out under a pressure ranging from atmospheric pressure to approximately 200 bars.

12. A process for triggering and/or carrying out chemical reactions by irradiating starting materials with short-wave electromagnetic radiation emitted from at least one substance sending out short-wave electromagnetic radiation upon irradiation and excitation with long-wave electromagnetic radiation under operating conditions, the short-wave electromagnetic radiation being generated in a closed vessel arranged within the starting materials and containing the short-wave electromagnetic radiation emitting substance, a low pressure gas being used as the short-wave electromagnetic radiation emitting substance, and ignition of the low pressure gas is caused by effecting an additional irradiation and excitation of a solid electrode in the closed vessel receiving the low pressure gas.

13. A process according to claim 12, wherein noble gases, methane, $CO_2$ and gases emitting carbon bands at 193 and 247 nm are used for the low pressure gas to generate the short-wave electromagnetic radiation.

14. A process for triggering and/or carrying out chemical reactions by irradiating starting materials with short-wave electromagnetic radiation emitted from at least one substance sending out short-wave electromagnetic radiation upon irradiation and excitation with long-wave electromagnetic radiation under operating conditions, the short-wave electromagnetic radiation being generated in a closed vessel arranged within the starting materials and containing the short-wave electromagnetic radiation emitting substance, and metal containing substances which, under said operating conditions, form volatile substances sending out said short-wave electromagnetic radiation upon irradiation and excitation with said long-wave electromagnetic radiation being used as the short-wave electromagnetic radiation emitting substance.

15. A process according to claim 14, wherein As, Bi, Cd, Cs, Ge, Hg, P, Pb, Rb, Sb, Se, Sn, Te, Tl or Zn are used as said metal containing substances.

* * * * *